(12) United States Patent
Lynch

(10) Patent No.: US 6,409,508 B1
(45) Date of Patent: Jun. 25, 2002

(54) USE OF OZONE FOR THE TREATMENT OF DENTAL CARIES

(75) Inventor: Edward Lynch, London (GB)

(73) Assignee: Natural White (CA)

( * ) Notice: Subject to any disclaimer, the term of this patent is extended or adjusted under 35 U.S.C. 154(b) by 0 days.

(21) Appl. No.: 09/700,275

(22) PCT Filed: Jun. 8, 1999

(86) PCT No.: PCT/EP99/04035

§ 371 (c)(1),
(2), (4) Date: Nov. 8, 2000

(87) PCT Pub. No.: WO99/64020

PCT Pub. Date: Dec. 16, 1999

(30) Foreign Application Priority Data

Jun. 8, 1998 (IE) ................................................. S980434

(51) Int. Cl.[7] ................................................. A61C 5/04
(52) U.S. Cl. ........................................................ 433/226
(58) Field of Search .................................. 433/226, 216, 433/88

(56) References Cited

U.S. PATENT DOCUMENTS

| 4,060,600 A | * | 11/1977 | Vit ............................... 424/53 |
| 4,438,100 A | * | 3/1984 | Balslev et al. ............... 424/104 |
| 4,743,199 A | * | 5/1988 | Weber et al. ................ 433/216 |
| 5,942,125 A | * | 8/1999 | Engelhard et al. .......... 210/748 |

FOREIGN PATENT DOCUMENTS

FR  2187288  *  1/1974

* cited by examiner

*Primary Examiner*—John J. Wilson
*Assistant Examiner*—Melba Bumgarner
(74) *Attorney, Agent, or Firm*—Walter A. Hackler

(57) ABSTRACT

This invention concerns the use of ozone in the treatment of dental caries.

28 Claims, No Drawings

USE OF OZONE FOR THE TREATMENT OF DENTAL CARIES

This invention relates to the use of ozone in the treatment of dental caries.

The great destructive disease of teeth is dental caries which may be defined as the acid dissolution of enamel, dentine or cementum as a consequence of the metabolism of micro-organisms living within deposits on the teeth known as plaque. Dental caries are believed to be associated with specific micro-organisms, the principal ones being Streptococcus Mutans, Lactobacilli, Actinomyces Visosus Serovar 2, Actinomyces Naeslundii and "Intermediate" Actinomyces, other Streptococci and yeasts. These are acid producing micro-organisms which produce acids such as acetic and lactic acids from the dietary carbohydrates. The micro-organisms associated with dental caries are unique and are ecologically very different from those associated with, for example, infected root canals.

Dental caries is currently managed by one or more of the following:

(i) preventive treatment by, for example, dietary and oral hygiene measures and may include the topical application of chemotherapeutic agents;

(ii) the removal of dentine exhibiting the signs of active caries;

(iii) the protection of any newly exposed non-carious dentine with restorative material.

Measures aimed at the prevention or the arrest of dental caries are mainly based on the elimination of dental plaque from the surfaces of roots and the institution of dietary controls to reduce the frequency and quantity of readily fermentable carbohydrate ingestion. The mechanical removal of plaque has been a major platform for the prevention of dental caries for some time. However, this poses special problems in the case of primary root caries due to access problems. Because dentine has a Knoop hardness of 68 in contrast to enamel at 11, the mechanical removal of plaque from its surface inevitably results in some loss of tissue also. Toothbrush abrasion is now a very common phenomenon and invariably leads to the loss of root dentine from the facial aspects of teeth. Consequently, the traditional methods of plaque control in the prevention of dental caries create further problems even when access permits it to be used effectively.

Conventional caries removal and cavity preparation entail the use of high and low speed handpieces. However, disadvantages of this system include the perception that drilling is unpleasant for patients and local anaesthetic is frequently required. Furthermore, handpieces are expensive to purchase and maintain and their use may lead to the removal of softened but uninfected dentine resulting in the excessive loss of tooth tissue.

Where restoration is required, all materials used to restore carious lesions have their limitations. For example, gold and ceramic are expensive and present a technical challenge for the practitioner. While amalgam is a durable, predictable material, it has poor aesthetic qualities, is potentially toxic and may cause allergic reactions in some people.

It is an object of the invention to alleviate the disadvantages of the prior art.

It has now unexpectedly been found that ozone can penetrate carious tissue and can therefore be used in the treatment of dental caries.

According to the present invention there is provided the use of ozone in the preparation of a therapeutic system for the treatment of dental caries.

As used herein, the term "ozone" is intended to embrace pure ozone, oxonised air and ozonised aqueous media, such as water optionally containing a reductant, such as thiocyanate or peppermint.

The ozone is delivered at a pressure sufficient to penetrate the carious tissue and at a concentration and for a period of time sufficient to kill substantially all of the micro-organisms within the carious lesion.

Preferably, a needle-sized jet of pure ozone or ozonised air in a shroud of micro-organism-free aqueous medium, e.g. water optionally containing a reductant, is injected at the desired location.

If desired, a sealant of the type known in the art may be applied to a carious lesion following ozone treatment.

The advantages of using ozone in the treatment of dental caries include the following:

1. It eliminates drilling and its attendant problems;
2. It is rapid and painless;
3. It does not require sophisticated methods of isolating the tooth;
4. No local anaesthetic is required.

The invention is illustrated in the following Examples. Unless otherwise stated, the ozone delivered in the following Examples is present in air at a concentration of 5.2%.

EXAMPLE 1

Many studies concerning the clinical evaluation of ozone have been based on assessments of its harmful effects rather than demonstrating any therapeutic benefits it may offer. Ozone is one of nature's most powerful oxidants which accounts for its ability to kill bacteria, spores and viruses. Uniquely, ozone decomposes to a harmless, non-toxic and environmentally safe material (oxygen). In this investigation, a multicomponent evaluation of the oxidative consumption of salivary biomolecules by ozone ($O_3$) has been performed using high resolution proton ($^1H$) nuclear magnetic resonance (NMR) spectroscopy. The ozone-generating equipment employed in this study was designed by Purezone Ltd. (Ipswich, U.K.). Unstimulated human saliva samples were collected from 8 patients and each of them was divided into two equivalent portions (0.60 ml). The first of these was treated with $O_3$ generated from the above device for a period of 30 seconds; the second group of portions served as controls. Samples were subjected to $^1H$ NMR analysis at an operating frequency of 600 MHz. Results acquired revealed that $O_3$ treatment gave rise to (1) the oxidative decarboxylation of the salivary electron-donor pyruvate (generating acetate and $CO_2$ as products), (2) oxidation of the volatile sulphur compound precursor methionine to its corresponding sulphoxide and (3) the oxidative consumption of salivary polyunsaturated fatty acids. Moreover, evidence for the $O_3$-mediated oxidation of salivary 3-D-hydroxybutyrate was also obtained. High field $^1H$ NMR spectroscopy provides much useful analytical data regarding the fate of $O_3$ in human saliva, information which is of much relevance to its potential therapeutic actions in vivo.

EXAMPLE 2

Ozone Effect on Microflora from Primary Root Caries Ex-vivo

Primary root carious lesions (PRCL) are a major clinical problem. The aim of this study was to establish if ozone could achieve effective microbial killing in PRCL. An ozone producing generator (Purezone Ltd., Ipswich, U.K.) was used in this ex-vivo study assessing the use of ozone on PRCL. In this study, soft PRCL requiring restoration were used as these are the most severe type of lesion found in humans. 20 freshly extracted teeth with PRCL requiring restoration were used. After plaque removal using a hand held standard fine nylon fibre sterile toothbrush with sterile water as a lubricant to cleanse the surface, each tooth was then isolated using sterile cotton wool rolls and dried using a dry sterile cotton wool roll. A sample of PRCL was taken using a sterile excavator from half of the most active part of the lesion. Subsequently, 10 seconds of the ozonised water was applied to the lesion and another sample was taken from the other half of the most active part of the lesion. Each sample was weighed and immediately placed in 1 ml of Fastidious Anaerobe Broth (FAB). To each 1 ml of FAB containing a biopsy of carious or ozone treated carious dentine, sterile glass beads were added. They were vortexed for 30 seconds to facilitate the extraction of any micro-organisms from the carious dentine and disperse any aggregates. After decimal dilution with FAB, 100 ml aliquots of these was spread on Fastidious Anaerobe Agar (LabM. Bury, Lancs., U.K.) supplemented with 5% (V/V) horse blood in an anaerobic chamber at 37° C. for four days. The mean±SE number of each colony type was counted and calculated.

|  | Before Ozone Treatment | After 10 Seconds of Ozone Treatment |
|---|---|---|
| Mean ± SE of total cfu ($Log_{10}$) | 5.91 ± 0.15 | 3.57 ± 0.37 |

Using the paired Student t-test a significant difference ($p<0.001$) was observed between the two groups. Clearly, the percentage of micro-organisms killed associated with the use of ozone was more than 99%.

EXAMPLE 3

Ozone Effect on Microflora from Primary Root Caries Ex-vivo

The procedure of Example 2 was repeated except that ozonised water was applied to the lesion for 20 seconds. Using the paired student t-test, a significant difference was observed in the ozonised water group ($log_{10}$ 3.77±0.42, mean±SE) compared with the control group ($log_{10}$ 6.18±0.21) ($p<0.001$).

The results of these tests show that the use of ozone can provide an effective, rapid and simple means for killing micro-organisms in carious lesions.

EXAMPLE 4

Sealant Shear Bond Strength to Sound and Carious Radicular Dentine

There has been little research on the interaction between primary root carious lesions (PRCL) and adhesive materials. The aim of this study was to examine the shear bond strength of four adhesive systems to PRCL with sound dentine acting as a control. The adhesive systems used were:
1. OptiBond FL Prime[1]/OptiBond FL Adhesive[1]/OptiGuard[1]
2. OptiBond FL Prime/OptiGuard
3. OptiGuard and
4. ChemFil II[2]

The materials were applied to sound radicular dentine and PRCL in vitro in freshly extracted teeth. The bonding site was macroscopically intact, was flat and had at least a 3.5 mm diameter. 37% phosphoric acid was used for 15 seconds in samples in groups 1→3 whilst 25% polyacrylic acid was used in group 4. After bonding the samples were stored for seven days in a moist atmosphere at 37° C. A shearing force was applied at 1 mm/minute. There were at least 10 samples in each group. The mean (s.e.) shear bond strengths were (MPa);

| Adhesive | Control | Carious |
|---|---|---|
| OptiBond FL Prime/OptiBond FL Adhesive/OptiGuard | 5.31 (1.03) | 5.58 (1.05) |
| OptiBond FL Prime/OptiGuard | 2.01 (0.59) | 1.63 (0.40) |
| OptiGuard | 0.73 (0.24) | 1.45 (0.52) |
| ChemFil II | 1.42 (0.28) | 1.01 (0.26) |

While statistical testing showed that the shear bond strength of the OptiBond FL Prime/OptiBond FL Adhesive/OptiGuard was significantly the highest, ($p<0.001$), the caries status of the root surface had no significant influence on the bond strength. OptiGuard in combination with OptiBond FL Prime and OptiBond Adhesive had the highest bond strength and this was not influenced by the caries status of the surface.

[1]Kerr, Romulus, Mich. U.S.A.;
[2]Dentsply, Konstanz, Germany.

EXAMPLE 5

The Effect of Ozone on Primary Root Caries and Associated Micro-organisms

The aims of these studies were to evaluate the efficiency of ozone on primary root caries and associated micro-organisms (*Streptococcus sobrinus*; TH 21, *Streptococcus mutans*; NCTC 10449). In study 1, 40 soft primary root carious lesions (PRCLs) from freshly extracted teeth were used and randomly divided into two groups to test the exposure to ozone for either 10 or 20 seconds. There was a significant ($p<0.001$) difference (Mean±SE) between the control samples for. either 10 seconds ($log_{10}$ 5.91±0.15) or 20 seconds ($log_{10}$ 6.18±0.21) and ozone treated samples for either 10 seconds ($log_{10}$ 3.57±0.37) or 20 seconds ($log_{10}$ 3.77±0.42). In study 2, 40 sterile saliva coated glass beads were put into bijoux bottles with 3 mls of Todd Hewitt broth for control and test groups. *S. sobrinus* and *S. mutans* were inoculated and incubated anaerobically overnight. Each glass bead was washed with 2 mls of PBS. Immediately, 10 seconds of ozone was applied to the glass beads in the test groups. Subsequently, each glass bead in the test and control groups was placed in 3 mls of Todd Hewitt Broth with six more sterile glass beads and were vortexed for 30 seconds. After decimal dilutions, 100 ml aliquots were spread on blood agar plates supplemented with 5% (V/V) horse blood and placed in an anaerobic chamber at 37° C. for two days. The number of each colony type was counted and calculated. Using the paired student t-test, there was a significant reduction ($p<0.0001$) (Mean±SE) between the control samples for *S. sobrinus* ($log_{10}$ 4.61±0.13) and *S. mutans* ($log_{10}$ 3.93±0.07) and ozone treated samples for *S. sobrinus* ($log_{10}$ 1.09±0.36) and *S. mutans* (log1.01±0.27). This treatment regime is therefore an effective, quick, conservative and simple method to kill micro-organisms in primary root carious lesions.

What is claim is:

1. A method of treating dental caries, the method comprising delivering ozone to the carious tissue at a pressure sufficient to kill substantially all of the micro-organisms within the carious tissue, without dissolving the carious tissue and without removal of the carious tissue following the ozone treatment.

2. The method according to claim 1 wherein the ozone is delivered for at least 0.5 second.

3. The method according to claim 1 wherein a needle-sized jet of pure ozone or ozonized air in a micro-organism-free aqueous medium is injected at the desired location.

4. The method according to claim 3 wherein the aqueous medium is water.

5. The method according to claim 3 wherein the aqueous medium contains a reductant.

6. The method according to claim 5 wherein the reductant comprises thiocyanate or peppermint.

7. The method according to claim 1 wherein a sealant is applied to the carious tissue following ozone treatment.

8. A method of treating dental caries, said method comprising the step of:

directing a stream comprising an oxidizing gas onto carious tissue for a period of time sufficient to kill microorganism within the carious tissue.

9. The method according to claim 8 wherein the step of directing a stream comprises directing a needle-sized jet of pure ozone.

10. The method according to claim 8 wherein the step of directing a stream comprises directing a needle-sized jet of ozonized air.

11. The method according to claim 10 wherein said ozonized air comprises about 5 percent ozone.

12. The method according to claim 10 wherein the stream includes a micro-organism-free aqueous medium.

13. The method according to claim 12 wherein the aqueous medium comprises a reductant.

14. The method according to claim 8 further comprises the step of applying a sealant to the carious tissue following the step of directing the stream of oxidizing gas onto the carious tissue.

15. A method of treating dental caries, said method comprising the step of;

penetrating carious tissue with gaseous ozone for a period of time sufficient to kill micro-organisms there within.

16. The method according to claim 15 wherein the ozone comprises a needle-sized jet of pure ozone.

17. The method according to claim 15 wherein the ozone comprises a needle-sized jet of ozonized air.

18. The method according to claim 17 wherein said ozonized air comprises about 5 percent ozone.

19. The method according to claim 17 wherein the ozone is mixed with a micro-organism-free aqueous medium.

20. The method according to claim 19 wherein the aqueous medium comprises a reductant.

21. The method according to claim 15 further comprising the step of applying a sealant to the carious tissue following the step of penetrating the carious tissue with gaseous ozone.

22. A method of treating root carious lesions, said method comprising the step of;

directing a stream comprising of gaseous ozone onto said primary root carious lesions for a period of time sufficient to kill micro-organisms within the carious tissue.

23. The method according to claim 22 wherein the step of directing a stream comprising gaseous ozone comprises directing a needle-sized jet of pure ozone.

24. The method according to claim 22 wherein the step of directing a stream comprising gaseous ozone comprises directing a needle-sized jet of ozonized air.

25. The method according to claim 24 wherein said ozonized air comprises about 5 percent ozone.

26. The method according to claim 24 wherein the stream includes a micro-organism-free aqueous medium.

27. The method according to claim 26 wherein the aqueous medium comprises a reductant.

28. The method according to claim 22 further comprising the step of applying a sealant to the primary root carious tissue following the step of directing the stream of gaseous ozone onto the carious tissue.

* * * * *